United States Patent [19]

Grabstein et al.

[11] Patent Number: 5,681,557
[45] Date of Patent: Oct. 28, 1997

[54] USE OF INTERLEUKIN-7 TO INDUCE MONOCYTES/MACROPHAGES CYTOTOXIC ACTIVITY

[75] Inventors: Kenneth H. Grabstein, Mercer Island; Mark Alderson, Bainbridge Island, both of Wash.

[73] Assignee: Sterling Winthrop Inc., New York, N.Y.

[21] Appl. No.: 440,807

[22] Filed: May 15, 1995

Related U.S. Application Data

[62] Division of Ser. No. 152,950, Nov. 12, 1993, Pat. No. 5,474,769, which is a continuation of Ser. No. 666,324, Mar. 8, 1991, abandoned.

[51] Int. Cl.$^6$ .................. C07K 14/54; A61K 38/20
[52] U.S. Cl. .................. 424/85.2; 514/2; 514/8; 514/885; 530/351
[58] Field of Search .................. 424/85.2; 514/2, 514/8, 885, 889; 530/351

[56] References Cited

U.S. PATENT DOCUMENTS

| | | | |
|---|---|---|---|
| 4,879,111 | 11/1989 | Chung | 424/85.2 |
| 5,032,396 | 7/1991 | Williams | 424/85.2 |
| 5,229,115 | 7/1993 | Lynch | 435/93 V |

OTHER PUBLICATIONS

Curti, B. D. (1993) Critical Reviews in Oncology/Hematology, vol. 14, pp. 29–39.
Jain, R. K. Scientific American, Jul. 1994, vol. 271, No. 1, pp. 58–65.
Jicha et al. (1991) J. of Euptal. Med. vol. 174 pp. 1511–1515.
Mc Bride et al. (1992) Cancer Res. vol. 52, pp. 3931–3932.
Moran et al., *Biol. Abst.* 96(6):AB–691, Ref. No. 65065, Sep. 1993.
Okazaki et al., "IL–7 Promoter Thymocyte Proliferation . . . ", *J. Immunol.* 143:2917–2922, 1989.
Stötter et al., "IL-7 Induces Human Lymphokine–Activated Killer Cell Activity . . . ", *J. Immunol.* 146:150–155, 1991.
Grabstein et al., *Science* 232:506–508, 1986.
Conlon et al., *Blood* 74:1368–1373, 1989.
Berkow et al., *The Merck Manual*, pp. 242–246, 1982.
Alderson et al., "Interleukin–7 Enhances Cytolytic T Lymphocyte Generation and Induces Lymphokine–activated Killer Cells from Human Peripheral Blood", *J. Exp. Med.* 172:577, 1990.
Armitage et al., "Regulation of Human T Cell Proliferation by IL–7", *J. Immunol.* 144:938, 1990.
Lynch et al., "Induction of Murine Lymphokine–Activated Killer Cells by Recombinant IL–7", *J. Immunol.* 154:1983, 1990.
Reed et al., "Recombinant Granulocyte/Macrophage Colony–Stimulating Factor Activates Macrophages to Inhibit *Trypanosoma cruzi* and Release Hydrogen Peroxide", *J. Exp. Med.* 166:1734, 1987.
Park et al., "Murine Interleukin–7 (IL–7) Receptor: Characterization on an IL–7–Dependent Cell Line", *J. Exp. Med.* 171:1073, 1990.
Tosoto et al., "Interleukin–7 Induces Interleukin–6 Production in Peripheral Blood Monocytes", *Blood* 75:1305, 1990.
Donnelly et al., "Differential Regulation of IL–1 Production in Human Monocytes by IFN–g and IL–4", *J. Immunol.* 145:569, 1990.

*Primary Examiner*—John Ulm
*Assistant Examiner*—Prema Mertz
*Attorney, Agent, or Firm*—William J. Davis; Imre Balogh

[57] ABSTRACT

There is disclosed a method of treating microbial infections in microbially infected mammals and a method of augmenting antitumor immunotoxicity in a mammal comprising administering a therapeutically effective amount of IL-7 in a pharmaceutically acceptable carrier. There is further disclosed a method of stimulating macrophages to produce cytokines made by activated macrophages and a method for improving T cell presentation by a macrophage comprising administering a therapeutically effective amount of IL-7. Further, antimicrobial activity of macrophages can be improved by administering a combination of IL-7 and Interferon-γ.

3 Claims, 4 Drawing Sheets

USE OF INTERLEUKIN-7 TO INDUCE MONOCYTES/MACROPHAGES CYTOTOXIC ACTIVITY

This application is a divisional of U.S. Ser. No. 08/152,950, filed Nov. 12, 1993, now U.S. Pat. No. 5,474,769 which is a continuation of U.S. Ser. No. 07/666,324, filed Mar. 8, 1991, now abandoned.

TECHNICAL FIELD OF THE INVENTION

The present invention relates to methods of increasing monocyte cytotoxicity directed against microbial infections, increasing monocyte cytotoxicity directed against tumor cells, by stimulating monocytes and macrophages with Interleukin-7 ("IL-7"). IL-7 exerts its effects on monocytes, in part, by activating monocytes to secrete Interleukin-6 (IL-6), Interleukin-1α (IL-1α), Interleukin-1β (IL-1β), Tumor Necrosis Factor-α (TNF-α), Interleukin-8 (IL-8), Macrophage Inhibitory Peptide-1α (MIP-1α), Macrophage Inhibitory Peptide-1β (MIP-1β), GRO (growth regulatory protein) and combinations thereof.

BACKGROUND OF THE INVENTION

Mammalian IL-7 had been previously designated "Lymphopoietin-1." The cloning and expression of human and murine IL-7 has been described in U.S. Pat. No. 4,965,195, issued on Oct. 23, 1990, the disclosure of which is incorporated by reference herein. IL-7 is a lymphopoietic growth factor that was first isolated and cloned by virtue of its ability to stimulate the growth of B- and T-cell progenitors in bone marrow. Published PCT Application WO 89/03884 (May 5, 1989) and EP-A-0314415 (May 3, 1989) disclose DNAs, vectors and related processes for producing IL-7 by recombinant DNA technology. The relevant disclosures of these published patent applications are incorporated by reference herein. The cloning of murine IL-7 was first reported in the scientific literature by Namen et al., *Nature* 333:571 (1988) and human IL-7 by Goodwin et al., *Proc. Natl. Acad. Sci. U.S.A.* 86:302 (1989). Purification of murine IL-7 from supernatants of transformed bone marrow stromal cells lines indicated an apparent molecular weight of approximately 25,000 daltons (see, e.g., Namen et al., *J. Exp. Med.* 16:7988 (1988)). The cDNA sequences reported by Namen et al. and Goodwin et al. suggest minimum molecular weights for murine and human IL-7 polypeptides of 14,897 and 17,387 daltons, respectively, exclusive of any glycosylation. Cloning, characterization and expression of IL-7 has enabled the characterization of its spectrum of biological activities.

IL-7 was originally defined by its ability to stimulate proliferation of pre-B cells (B220$^+$) derived from long-term bone marrow culture (Whitlock et al., *J. Immunol. Methods* 67:353–69 (1984)). IL-7 was unable, however, to stimulate proliferation of mature B cells or to induce differentiation of pre-B cells to surface Ig$^+$ cells (Lee et al., *J. Immunol.* 142:3875–83 (1989)).

Previous investigations with IL-7 suggested that only T lineage cells respond to this cytokine. For example, resting fetal and adult thymocytes of most surface phenotypes proliferate in response to IL-7 in a manner independent of Interleukin-2 (IL-2), Interleukin-4 (IL-4), or IL-6, Conlon et al., *Blood* 74:1368–73 (1989) and other references). Further, mature peripheral T cells respond to IL-7 in the presence of suboptimal mitogen concentrations (Chazen et al., *Proc. Natl. Acad. Sci. U.S.A.* 86:5923–27 (1989)). Morrissey et al., *J. Exp. Med.* 169:707–16 (1989) have shown that IL-7 can provide a co-stimulatory signal for the in vitro proliferative response of purified murine T cells to Con A by inducing IL-2 production. Additionally, Chazen et at., supra, have further shown that IL-7 in combination with PMA can directly stimulate T cell activation without intervention with another cytokine messenger. Response to a combination of IL-7 and PMA was not inhibited by high concentrations of neutralizing antibodies to either IL-2 or IL-4 and was largely resistant to immunosuppressive effects of CsA, a drug which inhibits the transcription of a number of lymphokine genes, including those encoding IL-2, IL-4 and Interferon-γ.

Many recent investigations utilizing IL-7 have focused upon T cell-mediated activity conferred by this cytokine. For example, Alderson et al., *J. Exp. Med.* 172:577–87 (1990) have shown that purified recombinant IL-7 can generate cytolytic T lymphocytes (CTL) in mixed lymphocyte culture. IL-7 was further shown to induce lymphokine-activated killer cells in autologous cultures of human peripheral blood mononuclear cells. The authors postulated that much of the IL-7 activity to induce CTL was accomplished via IL-2 production.

Park et al., *J. Exp. Med.* 171:1073–89 (1990) report that receptors for IL-7 have been demonstrated on lymphoid cells and myeloid lineage cells. However, no activity for IL-7 on monocytes/macrophages or neutrophils has been reported.

Other cytokines have been reported to stimulate macrophages or monocytes to produce a cytokine response. For example, Donnelly et al., *J. Immunol.* 145:569–75 (1990) report that the endotoxin LPS (lipopolysaccharide) stimulated monocyte production of IL-1β, TNF-α, and IL-6 and that cytokine production stimulated by endotoxin was inhibited by exposure of the macrophages to IL-4. Moreover, IL-4 was reported to suppress IL-1 production induced by a variety of monocyte activation stimuli, including LPS, PMA, and *Staphylococcus aureus*. Donnelly et al. further report that Interferon-γ, (IFN-γ) enhanced monocyte IL-1 production induced by LPS. IL-4 largely neutralized the potentiating effects of IFN-γ. Therefore, cytokines IFN-γ and IL-4 can influence the state of monocyte activation by either up-regulating (IFN-γ) or down-regulating (IL-4) the expression of IL-1.

IL-1 can further induce IL-6 production in peripheral blood monocytes. For example, Tosato et al., *Blood* 75:1305–10 (1990) reported that IL-6 production can be induced in monocytes by the endotoxin LPS, IL-1, TNF-α and Platelet-Derived Growth Factor (PDGF).

It appears that one of the primary functions of peripheral blood monocytes is to regulate synthesis and secretion of an array of biologically active molecules including enzymes, plasma proteins and cytokines. Monocyte-derived cytokines include IL-1α, IL-1β, IL-6, IL-8, and TNF-α. All of these cytokines, produced by monocytes, have broad immunoregulatory properties that are central to the host response to infection. Microbial products, such as LPS and peptidoglycan, are effective inducers of cytokine secretion by monocytes. More recently, monocyte-synthesized cytokines have been demonstrated to regulate monocyte cytokine synthesis. In particular, IL-1α, IL-1β, TNF-α, TGF-β, (Transforming Growth Factor-B) IFN-γ, GM-CSF and IL-3 have all been shown to stimulate some aspect of monocyte cytokine secretion, either acting alone or in combination with other stimuli, Conversely, IL-4 had potent antagonistic effects on the induction of monocyte activation, including both cytokine secretion and respiratory burst activity.

Accordingly, there is a need in the art to determine if IL-7 can affect monocyte function and whether IL-7 can be used to stimulate the antimicrobial, tumoricidal and cytokine-releasing activities of macrophages.

SUMMARY OF THE INVENTION

The present invention provides a method for treating microbial infections in a microbially-infected mammal comprising administering a therapeutically effective amount of IL-7 in a pharmaceutically acceptable carrier. The microbial infection may be caused by a microbe or a group of microbes selected from the group consisting of gram negative bacteria, gram positive bacteria, yeast, fungi, viruses and protozoa. The present invention further provides a method for augmenting antitumor cytotoxic activity in a mammal in need of antitumor therapy comprising administering a therapeutically effective amount of IL-7 in a pharmaceutically acceptable carrier. The present invention further provides methods of stimulating macrophages in a mammal to produce cytokines, wherein the monocyte-synthesized cytokines are selected from the group consisting of IL-6, IL-1α, IL-1β, TNF-α, IL-8, MIP-1α, MIP-1β, GRO, and combinations thereof. Further, IL-7 can improve macrophage and monocyte cell function to present antigen to T cells to further enhance cytolytic abilities of T lymphocytes. Moreover, IL-7 stimulation of macrophages and monocytes can augment antitumor immunotoxicity in a susceptible mammal.

We have discovered that IL-7 stimulated the secretion of monocyte-synthesized cytokines, including IL-6, IL-1α, IL-1β, and TNF-α in purified human peripheral blood monocytes and also enhanced monocyte/macrophage tumoricidal activity. These results implicate IL-7 as an important regulator of inflammation by inducing the secretion of cytokines that are central to the inflammatory process.

BRIEF DESCRIPTION OF THE DRAWING

As shown in FIG. 2, low levels of IL-6 were detectable in the supernatants of IL-7, IL-1β or LPS-stimulated monocytes as early as two hours after the initiation of culture stimulation. All three stimuli showed similar kinetic profiles of IL-6 induction.

DETAILED DESCRIPTION OF THE INVENTION

Figure 1A:
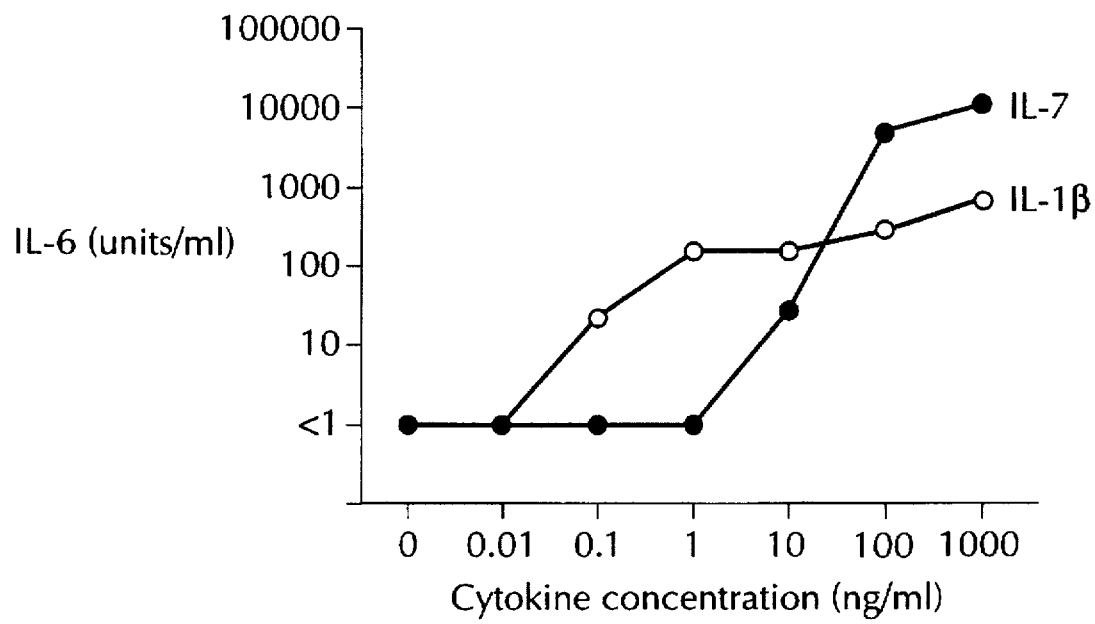
FIGS. 1A and 1B show an IL-7 and IL-1β dose response comparison for IL-6 secretion, induced by IL-7 or IL-1β, in human peripheral blood monocyte culture (PBMC). IL-6 secretion was assessed by either a B9 hybridoma growth factor assay (FIG. 1A) or by an ELISA (FIG. 1B). These data show that IL-7 induced significant IL-6 production when used in concentrations of 10 ng/ml or greater, although optimal IL-7 activity was observed at 100 ng/ml. Identical results were obtained when IL-6 was assayed by either the B9 assay or by ELISA. IL-1β also induced IL-6 secretion.

The present invention provides methods of treating microbial infections, stimulating macrophages to produce cytokines made by activated macrophages, improving macrophage presentation to T cells, and augmenting antitumor immunotoxicity in a mammal comprising administering a therapeutically effective amount of IL-7. IL-7 is, preferably, formulated in a pharmaceutically acceptable carrier. The present invention further comprises a method of treating microbial infections with a combination of IL-7 and IFN-g. For treatment of humans, IL-7 is preferably a human IL-7. Preferably, IL-7 is produced by expression of a nucleotide sequence which hybridizes to a native human IL-7 cDNA sequence, as described in U.S. Pat. No. 4,965,195. Preferred hybridization conditions are high stringency conditions. IL-7 derivatives and analogs are further characterized by the ability to demonstrate IL-7 biological activity as measured by, for example, a murine pre-B cell assay described in U.S. Pat. No. 4,965,195.

When a microbially-infected mammal harbors an invading pathogen (microbe), a microbial infection may result. The microbial infection may be caused by one or a plurality of microbes selected from the group consisting of gram negative bacteria, gram positive bacteria, yeast, fungi, viruses and protozoa. Applicants have studied *Trypanosoma cruzi* (*T. cruzi*) which is a common Third World protozoan infection. *T. cruzi* is the etiologic agent of Chagas' Disease. *T. cruzi* replicates in the cytoplasm of mononuclear phagocytes. Like many other infections caused by protozoa and other microbial sources, factors released by antigen- or mitogen-stimulated T lymphocytes can activate macrophages to inhibit growth of *T. cruzi* or any other infectious agents. Therefore, macrophage activation is an integral component of the immune response to microbial infection. Other invading microbial pathogens include, for example, fungi, yeast, other protozoa, and bacteria such as Salmonella (typhimurium, dublin, abortusovis, abortivoequina, gallinarum, choleraesuis, typhi), *Shigella flexneri* and *Shigella sonnei*, *Tubercle basilli* and *Leprosy basilli*. Other microbial infections that can be treated by enhancing monocyte/macrophage function include the bacteria *Corynebacterium diphtheriae* (non-invasive pharyngitis), *Vibrio cholerae* (non-invasive enteritis), *Neisseria meningitidis* (nasopharynx bacteraemia or meningitis) *Staphylococcus aureus* (locally invasive), *Mycobacterium tuberculosis* (invasive locally, toxic and hypersensitivity), *Mycobacterium leprae* (invasive), *Listeria monocytogenes*, *Salmonella typhimurium*, *Chlamydia psittaci*, *Chlamydia trachomatis* and *Legionella pneumophillia*. Other microbial infections that can be treated by enhancing monocyte/macrophage function are caused by protozoa, fungi, Helminths, and Rickettsia. Examples of protozoa include *Toxoplasma gondii*, *Leishmania donovani*, *Leishmania mexicana*, *Leishmania major*, and *Trypanosoma cruzi*. An example of a Helminths infection is one caused by *Schistosoma mansoni*. Treatable fungal infections are caused by *Histoplasma capsulatum*, *Candida albicans*, *Candida parapsilosis*, and *Cryptococcus neoformans*. The Rickettsia include, for example, *R. prowazekii*, *R. coronii*, and *R. tsutsugamushi*.

IL-7 activation of macrophages and IFN-γ activation of macrophages can enhance macrophage response to any invading microbe. The combination of IL-7 and IFN-γ appears to exert a synergistic effect upon macrophage activation and subsequent antimicrobial and antitumor activity.

The present invention provides a method of treating microbial infections in a microbially-infected mammal, a method of improving macrophage antigen presentation to T cells, a method for augmenting antitumor immunotoxicity in a mammal, and a method for stimulating macrophages in a mammal (in vivo) or in vitro. The present inventive methods all relate to the ability of IL-7 to act upon macrophages, such as peripheral blood monocytes.

Based upon in vitro data, when IL-7 was added to PBMC or purified monocytes, it was found to stimulate the secretion of high levels of IL-6, IL-1α, IL-1β, and TNF-α. IL-7 also induced monocyte/macrophage mediated lysis of a A375 human melanoma cell line, which is a model system for determining antitumor cytotoxicity. These data, using in vitro model systems, demonstrate the antimicrobial and antitumor properties of IL-7. These data indicated that the antimicrobial and antitumor properties of IL-7 are mediated through macrophage/monocyte vehicles.

As used herein, the term "IL-7" means IL-7 polypeptides and derivatives and analogs thereof having substantial amino acid sequence identity to native mammalian IL-7s and substantially equivalent biological activity, e.g., in standard bioassays or assays of IL-7 receptor binding affinity. As used herein, the term "IFN-γ" means IFN-γ polypeptides and derivatives and analogs thereof having substantial amino acid sequence identity to native mammalian interferon-gamma and substantially equivalent biological activity in standard bioassays or assays of IFN-γ receptor binding. IFN-γ is described, for example, in U.S. Pat. No. 4,851,219, the disclosure of which is incorporated by reference herein. IFN-γ is a well characterized cytokine which may be obtained in homogeneous dosage forms from recombinant or native sources. Any source of IFN-γ is acceptable so long as the IFN-γ is in a physiologically acceptable vehicle or excipient and it is species compatible, e.g., human IFN-γ should be used in the therapy of humans. Amino acid sequence variants of IFN-γ or IL-7 are useful so long as they exhibit the biological activity of IFN-γ or IL-7 respectively.

Preferred methods for producing mammalian IL-7s involve expression in mammalian cells, although recombinant proteins can also be produced using insect cells, yeast, bacteria, or other cells under the control of appropriate promoters. Appropriate cloning and expression vectors for use with bacterial, fungal, yeast and mammalian cellular hosts are described in Pouwels et al., *Cloning Vectors: A Laboratory Manual* (Elsevier, New York 1985).

Examples of pharmaceutically acceptable carriers include excipients and diluents, such as neutral buffered saline or saline mixed with conspecific serum albumin. The formulation is preferably lyophilized using appropriate excipient solutions, such as sucrose as diluents. The appropriate dosages for administration of IL-7 or IFN-γ are within the range of about 10 ng/kg/day to about 100 µg/kg/day each or in combination. Preferably a dose of 100 ng/kg/day to about 1000 ng/kg/day for 1–20 days can be expected to induce an appropriate biological effect. Alternatively, bolus injections of from about 1 µg/kg/day to about 100 µg/kg/day can be given at approximately 4-day intervals to exert either antimicrobial or antitumor effects via augmentation of immunotoxicity pathways mediated by macrophages/monocytes.

Mammals needing treatment for a microbial infection or for a tumor are administered effective amounts of IL-7 either alone or in the form of a pharmaceutical composition. Pharmaceutical compositions of the present invention comprise IL-7 formulated into compositions together with one or more non-toxic physiologically acceptable carriers, adjuvants or vehicles which are collectively referred to herein as carriers, for parenteral injection, for oral administration in solid or liquid form, for rectal or topical administration and the like. The pharmaceutical composition may further comprise IFN-γ. The compositions can be administered to humans and/or animals either orally, rectally, parenterally (intravenously, intramuscularly, or subcutaneously), intracisternally, intravaginally, intraperitoneally, locally, or as buccal or nasal spray. Compositions suitable for parenteral injection may comprise physiologically acceptable sterile aqueous or non-aqueous solutions, dispersions, suspensions or emulsions in sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and the use of surfactants.

These compositions may also contain adjuvants such as preserving, wetting, emulsifying, and dispensing agents. Preservation of the action of microorganisms can be insured by various antibacterial and antifungal agents (e.g., parabens, chlorobutanol, phenol, sorbic acid, and the like). It may also be desirable to include isotonic agents (e.g. sugars, sodium chloride and the like). Prolonged absorption of the injectable pharmaceutical form can be brought about by the use of agents delaying absorption (e.g., aluminum monosterate and gelatin).

If desired, in far more effective distribution, the compounds can be incorporated into slow release or targeted delivery systems, such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

IL-7 can also be administered in the form of liposomes. As is known in the art, liposomes are generally derived from phospholipids or other lipid substances. Liposomes are formed by mono- or multi-lamellar hydrated liquid crystals that are dispersed in an aqueous medium, and a non-toxic physiologically acceptable and metabolizable lipid capable of forming liposomes can be used. IL-7 in liposome form can contain, in addition to IL-7, stabilizers, preservatives, excipients and the like. The preferred lipids are the phospholipids and the phosphatidyl cholines (lecithins), both natural and synthetic.

The activity of IL-7 on monocyte cytokine secretion resembles the biological activity of a bacterial endotoxin. We investigated whether the results attributed to IL-7 were actually the results of endotoxin contamination of the IL-7 cytokine preparation. endotoxin contamination was a remote possibility because the cytokines were extensively purified and the particular preparations used in the examples reported herein were selected on the basis of their low endotoxin content (<1 pg/µg of protein). However, we also checked to make sure that the biological activity we observed was not the result of endotoxin contamination. We heated IL-7 to denature the polypeptide. We investigated whether heated IL-7 can stimulate IL-6 secretion. We found that denaturing IL-7 by heating (100° C. for 30 minutes) totally removed its ability to stimulate IL-6 secretion and IL-6 mRNA. By contrast, heating LPS (and endotoxin) to 100° C. for 30 mutes did not affect its ability to stimulate IL-6 production in monocytes. Denatured IL-7, at concentrations up to 1 µg/ml, was unable to induce IL-6 secretion by the THP-1 monocytic cell line. LPS (an endotoxin) is a potent inducer of IL-6 by these cells. Therefore, these data support the conclusion that macrophage/monocyte biological activity attributed to IL-7 was not due to bacterial endotoxin contamination.

The data presented herein indicate that IL-7 signals differently to T cells and monocytes. IL-4 does not inhibit the IL-7-induced proliferation of CTL generation (cytotoxic T lymphocyte) of T cells. However, IL-4 did inhibit IL-7-induced expression of IL-6 in macrophage cultures and human MIP-1β gene expression in monocytes. The data presented herein indicate that IL-7 induces IL-1, IL-6 and TNF-α and these data suggest the IL-7 is a mediator of immune inflammatory responses. These data further indicate that IL-7 is and important mediator of the host response to tumor antigens, microbial infections, and particularly viral infections. Thus, these data gathered from various antimicrobial and antitumor in vitro models support the present invention that IL-7 stimulates macrophages/monocytes to mediate antimicrobial and antitumor activity in a mammal in need of such treatment.

The following examples illustrate in vitro models for the antimicrobial activity and tumoricidal activity mediated by IL-7. This activity was inhibited by IL-4.

EXAMPLE 1

This example illustrates how monocyte/macrophage cultures were obtained, and further illustrates the ability of IL-7 to induce IL-6 secretion in activated monocytes. Monocytes from peripheral blood monocyte culture (PBMC) were isolated from heparinized human blood by centrifugation over Ficoll-Hypaque. Monocytes were enriched by countercurrent elutriation of PBMC followed by adherence to plastic to form an enriched monocyte population of $2\times10^5$ cells in 1 ml of culture medium in 16-mm wells (3524; Costar Cambridge Mass.). After 90 minutes of incubation at 37° C., non-adherent cells were removed by gentle washing and replaced with fresh culture medium. The elutriated cells were 90–95% monocytes (as determined by microscopic examination of Giemsa-stained cytospin preparations) and 80–85% $CD14^+$ (a cell surface marker expressed on a majority of monocytes) cells as determined by flow cytometry. Culture medium consisted of low endotoxin RPMI 1640 (Whittaker Bioproducts, Walkersville, Md.) supplemented with 10% low endotoxin FCS (Cellect Gold Flow Laboratories, McLean, Va.), 50 U/ml penicillin, 50 µg/ml streptomycin, and $5\times10^{-5}$ M 2-ME (2-Mercaptoethanol).

The cytokine preparations used herein contained less than 1 pg of endotoxin per µg of protein, except IL-1α which contained 3 pg/µg protein. Endotoxin was assayed by a Limulus amebocyte lysate assay (Whittaker).

IL-7 was purified from *E. coli* expressing a human IL-7 cDNA as described in U.S. Pat. No. 4,965,195. IL-7 had a specific activity of $3\times10^4$ U/µg in a murine pre-B cell assay. IL-1α and IL-1β were purified from *E. coli* expressing human IL-1α or IL-1β cDNAs as described in Kronheim et al., *Bio/Technology* 4:1078 (1986) and had specific activities of $1.9\times10^6$ U/µg and $2.2\times10^6$ U/µg, respectively, as determined in a thymocyte costimulation assay. IL-4 was purified from supernatant of yeast cells expressing a human IL-4 cDNA. IL-4 had a specific activity of $10^4$ U/µg in a B cell comitogenesis assay. Granulocyte-macrophage colony stimulating factor (GM-CSF) was purified from yeast cells expressing a human GM-CSF cDNA. The specific activity of human GM-CSF was $5\times10^4$ U/µg as determined by a human bone marrow proliferation assay. *Salmonella typhimurium* LPS (Difco Laboratories, Detroit, Mich.) was used at a concentration of 10 µg/ml.

We determined whether IL-7 can stimulate IL-6 secretion in human PBMC. PBMC were cultured in either mixed lymphocyte cultures (MLC) or autologous cultures in the presence of medium alone, purified human recombinant IL-7 at 50 ng/ml or LPS at 10 µg/ml. After 24 hours, culture supernatants were recovered and assessed for the presence of IL-6. IL-6 activity was assayed by the ability of culture supernatants to cause proliferation of an IL-6-dependent B9 Hybridoma Cell Line, as described in Arden et al., *Eur. J. Immunol.* 17:1411 (1987). Briefly, the procedure obtains thrice washed B9 cells and adds the B9 cells to serial dilutions of test supernatants in 0.2 ml of RPMI 1640 (Gibco Laboratories, Grand Island, N.Y.), supplemented with 10% FCS (Fetal Calf Serum, Hyclone Laboratories, Logan, Utah) in 96 well flat bottom plates (Costar). Samples were assayed in duplicate. After three days, B9 cell proliferation was assessed by tritiated thymidine (1 µCi/well) incorporation during a six hour incubation. One unit of IL-6 is defined as the amount required for half maximal stimulation of B9 cell proliferation.

IL-6 was also assessed by an ELISA assay with a monoclonal antibody specific for human IL-6. ELISA plates (Corning Glass Works, Corning, N.Y.) were coated overnight at 4° C. with 5 µg/ml of a murine MAb against human IL-6. After blocking with a 5% solution of non-fat dry milk in PBS (phosphate buffered saline), test supernatants were serially diluted in PBS with 10% goat serum and incubated for one hour at room temperature. The plates were washed. A rabbit antiserum raised against human IL-6 was added to each well at a 1:1000 dilution in PBS/20% goat serum. After a further hour of incubation at room temperature the plates were thoroughly washed and a horseradish peroxidase-coupled goat anti-rabbit Ab (Sigma Co., St. Louis, Mo.) at 1:2000 dilution in PBS/5% non-fat dry milk was added. After washing, the substrate (3,3',5,5'-tetramethyl benzidine (TMB), Kirkegaard & Perry, Gaithersburg, Md.) was added. Absorbance was determined at one hour using a Dynatech ELISA reader. IL-6 concentrations in test samples were determined by comparing titration curves with titrations of a standard human IL-6 preparation (R & D Systems, Minneapolis, Minn.) using a Deltasoft 1.8 ELISA analysis program (Biometallics, Inc., Princeton, N.J.).

Cultures of PBMC or MLC in medium alone contained no detectable IL-6 activity (limit of detection less than 1.0 units/ml), whereas similar cultures supplemented with either IL-7 or LPS contained high levels of IL-6. The cultures were established with about $10^6$ responding cells and either $10^6$ irradiated autologous filler cells (autologous cultures) or about $10^6$ irradiated allogeneic stimulator cells (MLC). Cultures were either non-supplemented or supplemented with 50 ng/ml IL-7 at the initiation of culture and supernatants collected after 24 hours and assayed for the presence of IL-6 bioactivity by the B9 hybridoma growth factor assay. The data are presented in Table 1 below.

TABLE 1

IL-7 Induces IL-6 Secretion in MLC and in Autologous PBMC Cultures

| Stimulus | IL-6 (U/ml) | | | |
|---|---|---|---|---|
| | Autologous | | MLC | |
| | Exp. 1 | Exp. 2 | Exp. 1 | Exp. 2 |
| Medium (control) | <1 | <1 | <1 | <1 |
| IL-7 | 1109 | 1211 | 1270 | 942 |
| LPS | — | 6976 | — | 7684 |

These data show that the presence of alloantigen in MLC neither enhanced nor inhibited the ability of IL-7 to induce IL-6 production in the 24 hour test period. Because IL-6 secretion by PBMC (particularly monocytes) is exquisitely sensitive to endotoxin, all the reagents used herein were selected for their low endotoxin levels. In addition, we found that heating IL-7 to 100° C. for 30 minutes totally abolished IL-7s activity to induce IL-6 secretion by PBMC. Heating LPS to 100° C. for 30 minutes had no effect on its activity.

EXAMPLE 2

This example illustrates activation of monocytes to secrete IL-7 by IL-7, IL-1α and IL-1β. Monocytes, T cells and B cells have all been shown to secrete IL-6. However, only monocytes appear to represent a major cellular source of IL-6 in human peripheral blood. In order to determine which cells were being stimulated by IL-7 to secrete IL-6, we separated PBMC into populations enriched for monocytes and T cells, or monocytes and lymphocytes. Table 2 below shows the results of two experiments. Experiment 1 provides a population enriched for monocytes and T cells. Experiment 2 provides a population of monocytes and lymphocytes.

The cells were divided into lymphocyte and monocyte-enriched fractions by counter-current elutriation, based upon microscopic examination of Giemsa-stained cytospins. In Experiment 1, the lymphocyte fraction was further enriched for T cells by E-resetting. In Experiment 2, 5h3 lymphocyte fraction was depleted of monocytes by two cycles of plastic adherence. The monocyte fraction, after further enrichment by plastic adherence, contained 90–95% monocytes (as determined by examination of Giemsa-stained cytospins), and 80–90% $CD14^+$ cells (as determined by flow cytometry). The lymphocyte fraction contained less than 1% $CD14^+$ cells.

TABLE 2

| | Experiment 1 | | | Experiment 2 | | |
|---|---|---|---|---|---|---|
| Stimulus | PBMC | Monos | T cells | PBMC | Monos | lymphocytes |
| Medium | 19 | 15 | <1 | <1 | <1 | <1 |
| IL-1α | ND | ND | ND | 654 | 894 | 40 |
| IL-1β | ND | ND | ND | 272 | 276 | 10 |
| IL-7 | 3067 | 5654 | 11 | 1895 | 2437 | 49 |
| LPS | ND | ND | ND | 1353 | <10000 | 107 |

The data in Table 2 demonstrate that, following stimulation with IL-7, IL-1α, IL-1β or LPS, the vast majority of IL-6 activity is secreted by the monocyte-enriched population. There was little IL-6 activity derived from lymphocyte or T cell populations. However, T cells did secrete IL-6 after five days of incubation with PMA plus PHA, as reported previously (Horii et al., *J. Immunol.* 141:1529 (1988)). LPS was found to be the most potent stimulus for monocyte IL-6 production, followed by IL-7, IL-1α, and then IL-1β.

EXAMPLE 3

This example illustrates the effects of IL-7 on IL-6 gene expression in monocytes. IL-6 mRNA levels were assessed by Northern analysis after culturing monocytes with various stimuli for four hours. Northern analysis of IL-6 mRNA was determined as follows: (1) Total cellular RNA was isolated as described in Chromazynski et al., *Anal. Biochem.* 162:156 (1987); (2) prehybridization was accomplished by separating ten micrograms of RNA on 1% agarose/6% formaldehyde gels, transferring to nylon filters (Hybond Amersham) and staining with methylene blue to insure equal loading in each lane; (3) after prehybridization, the filters were hybridized at 63° C. in a buffer containing 5× SSC/10× Denhardt's/50% formamide for 18 hours; (4) the filters were washed, first in 1× SSC/0.1% SDS, then 0.1× SSC/0.1% SDS, at 68° C. The filters were then subjected to autoradiography to determine IL-6 mRNA levels.

We found that IL-7, IL-1α, IL-1β and LPS all stimulated significant IL-6 mRNA accumulations in monocytes. Control cells cultured in medium alone did not contain detectable IL-6 mRNA. These data agree with the data in Example 2 (Table 2). The level of IL-6 mRNA expression induced by IL-7 was greater than that induced by IL-β.

EXAMPLE 4

Figure 1B:
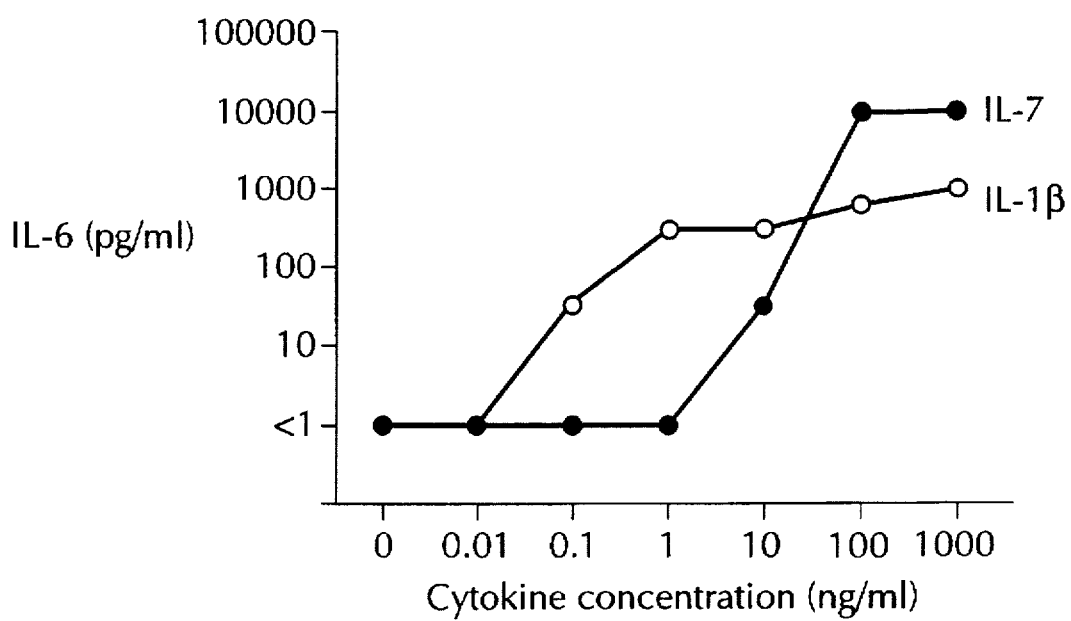

This example illustrates a comparison of the activities of IL-7 and IL-β to induce IL-6 secretion in monocytes. FIG. 1a shows IL-6 levels assessed by the B9 Hybridoma Growth Factor Assay and FIG. 1b shows IL-6 levels as assessed by an ELISA assay. IL-7 induced significant IL-6 production when used at concentrations of 10 ng/ml or greater, though optimal IL-7 activity was observed at 100 ng/ml. IL-1β, by contrast, had a significant effect on IL-6 secretion at 0.1 ng/mg. These data are in agreement with data presented in Tosato et al., *Blood* 75:1305 (1990). Optimal concentrations of IL-7 induced approximately 10-fold higher levels of IL-6 than optimal concentrations of IL-1β (FIGS. 1A and 1B). Identical results were obtained when IL-6 was assayed by either the B9 assay (biological activity) or the ELISA.

EXAMPLE 5

This example illustrates a comparison of the concentration of IL-7 required to stimulate T cells or monocytes. The same preparation of IL-7 was used for both T cells and monocytes. T cell activity was determined by assaying for enhancement of CTL generation in human mixed lymphocyte cultures (MLC). Monocyte activation was assessed by determining IL-6 secretion. Both Armitage et al., *J. Immunol.* 144:938 (1990) and Alderson et al., *J. Exp. Med.* 172:577 (1990) have shown that IL-7 co-stimulates the proliferation of human T cells and enhances CTL generation at concentrations as low as 0.1 ng/ml. As shown in Example 4 above and in FIGS. 1A and 1B, 10 ng/ml or more of IL-7 was required for induction of IL-6 secretion and an optimal effect was seen with 100 ng/ml of IL-7. Table 3 (below) shows that as little as 0.1 ng/ml of IL-7 could enhance CTL generation and maximal effects were seen with 10 ng/ml of IL-7.

TABLE 3

| IL-7 (ng/ml) | CTL Activity % Lysis | Monocyte Activity IL-6 (U/ml) |
|---|---|---|
| 0 | 0.3 | <1 |
| 0.1 | 8.9 | <1 |
| 1 | 30 | <1 |
| 10 | 61 | 1920 |
| 100 | 47 | 5923 |
| 1000 | NT | 7867 |

Thus, CTL precursors appear to display approximately 100-fold greater sensitivity to IL-7 than monocytes.

EXAMPLE 6

Figure 2:
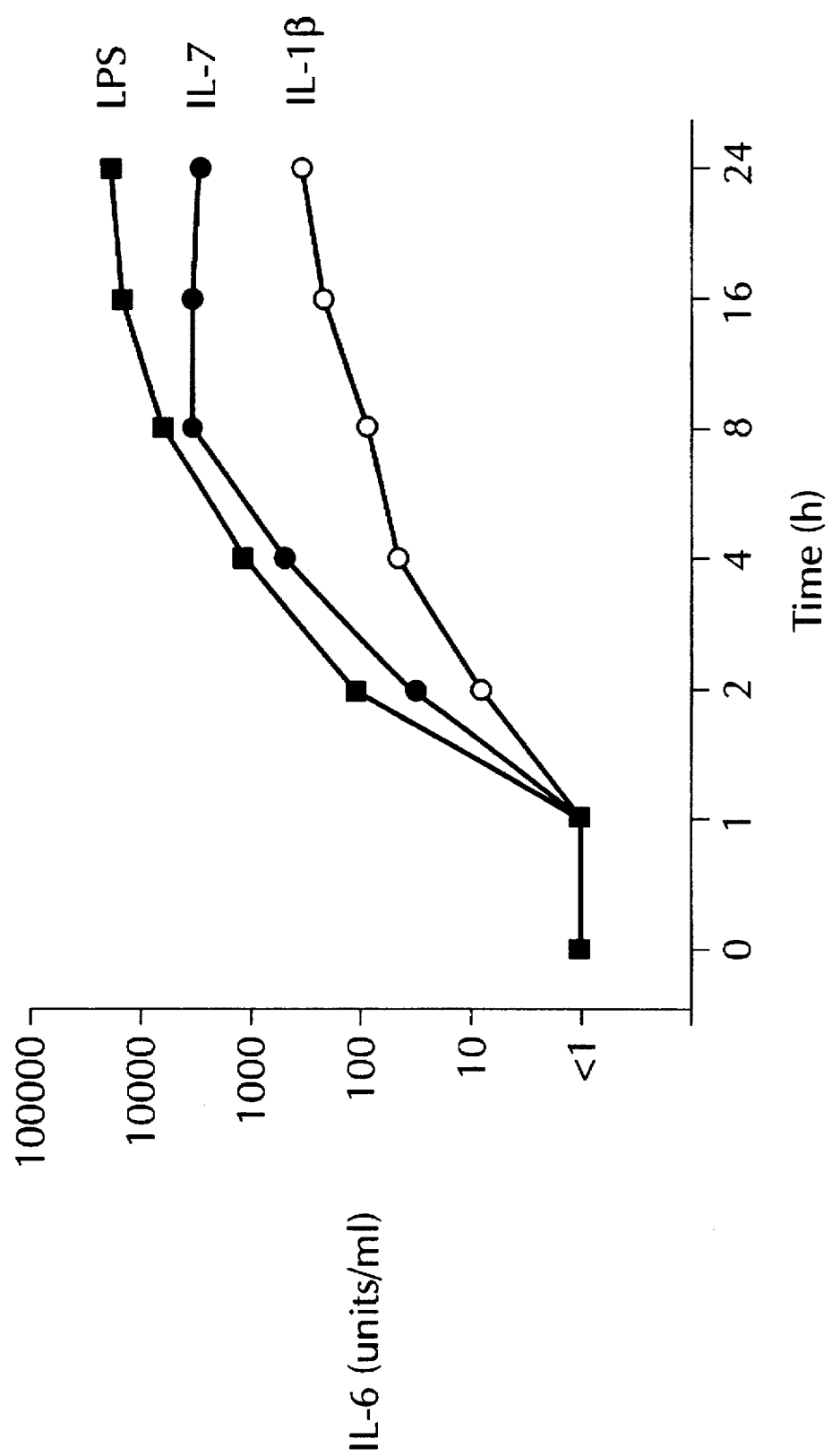
FIG. 2 illustrates kinetice of IL-6 secretion from PBMC after various culture periods when stimulated with optimal concentrations of either IL-7, IL-1β, or LPS.

This example determines kinetics of IL-6 induction in monocytes by IL-7. Monocytes were stimulated with optimal concentrations of IL-7, IL-1β or LPS. Supernatants were collected at various timepoints after stimulation and assayed for IL-6 activity according to the B9 cell assay described in Example 1. As shown in FIG. 2, low levels of IL-6 were detectable in the supernatants of IL-7, IL-1β or LPS stimulated monocytes as early as two hours after the initiation of culture. IL-6 was not detected in non-stimulated cultures at any timepoint. All three stimuli showed similar kinetic profiles of IL-6 induction. Optimal levels of IL-6 were detected within 24 hours. Again, IL-7 was found to be a more potent inducer of IL-6 secretion than IL-1β.

EXAMPLE 7

This example illustrates the ability of IL-4 to inhibit IL-6 secretion-inducing activity and IL-6 mRNA formation by IL-7 in monocytes. IL-4 had previously been observed to inhibit the ability of IL-7 to induce LAK activity in PBMC cultures (Alderson et al..) We cultured purified monocytes with IL-7 or LPS, either alone or in the presence of IL-4. IL-7 was provided at a concentration of 100 ng/ml, LPS at a concentration of 10 µg/ml. IL-4 was provided at concentration of 50 ng/ml in Experiment 1, and 100 ng/ml in Experiment 2. The supernatants were collected after 36 hours, and assayed for IL-6 activity in the B9 cell assay. The results are presented in Table 4.

TABLE 4

| Stimulus | Experiment 1 | | Experiment 2 | |
|---|---|---|---|---|
| | −IL-4 | +IL-4 | −IL-4 | +IL-4 |
| Medium | <1 | <1 | <1 | <1 |
| IL-7 | 19,220 | 3,665 | 2,437 | 106 |
| LPS | 16,343 | 6,176 | 10,143 | 1,502 |

As shown in Table 4, IL-4 was found to markedly inhibit the ability of either IL-7 or LPS to promote IL-6 secretion (mean of 88% and 74% inhibition, respectively). Suppression of IL-7 induced IL-6 secretion could be seen at concentrations of IL-4 as low as 0.1 ng/ml (data not shown in Table 4). The inhibitory effects of IL-4 on IL-6 secretion were also apparent at the mRNA level (data not shown in Table 4). Therefore, the addition of IL-4 to monocytes stimulated with either IL-7 or LPS significantly downregulated IL-6 mRNA and IL-6 secretion.

EXAMPLE 8

This example illustrates the ability of IL-7 to induce IL-1α, IL-1β and TNF-α secretion by monocytes. Monocytes were cultured for 36 hours with various concentrations of IL-7 or with 10 µg/ml of LPS. Cultured monocyte supernatants were collected and assessed for the presence of IL-1α, IL-1β, IL-6 and TNF-α by cytokine-specific ELISAs. Table 5 (below) shows that supernatants from monocytes cultured with medium alone or up to 10 ng/ml of IL-7 do not contain detectable amounts of all four cytokines assayed. The limit of detection was from about 1 pg/ml to about 5 pg/ml. However, 100 ng/ml or greater IL-7 induced significant secretion of IL-1α, IL-1β, IL-6 and TNF-α by monocytes. Optimal concentrations of IL-7 induced greater than 100-fold increases in the production of all three cytokines by cultured monocytes.

TABLE 5

| | Cytokine production (pg/ml) | | | |
|---|---|---|---|---|
| IL-7 (ng/ml) | IL-1α | IL-1β | IL-6 | TNFα |
| 0 | <1 | <5 | <3 | <2 |
| 0.1 | <1 | <5 | <3 | <2 |
| 1 | <1 | <5 | <3 | <2 |
| 10 | <1 | <5 | <3 | <2 |
| 100 | 202 | 1572 | 8964 | 1050 |
| 1000 | 527 | 2586 | 12714 | 1170 |
| LPS | 372 | 2860 | 11606 | 2370 |

EXAMPLE 9

This example illustrates the ability of IL-7 to induce monocyte/macrophage tumoricidal activity. Monocytes can be stimulated by LPS and certain cytokines, such as GM-CSF, in vitro to become cytotoxic for selected tumor cell lines (Grabstein et al., Science 232:506 (1986)). More specifically, Grabstein et al. described the ability of activated cultured monocytes to lyse a human melanoma cell line called A375. This example examines the ability of IL-7 to induce monocyte/macrophage tumoricidal cytotoxicity against the A375 human melanoma cell line. This is an in vitro model for IL-7 anti-tumor activity.

Target A375 cells were labeled for 24 hours with tritiated thymidine. The labeled A375 cells were added to 24 hour monocyte cultures. After 24 hours, culture supernatants were removed and replaced with fresh medium, and then cultured for an additional 48 hours. The cultures were then washed twice with medium and the cells were lysed with 0.1% NP40 in PBS. Lysed cells were harvested for liquid scintillation (Beta) counting. Percent cytotoxicity was calculated from the following formula:

$$\% \text{ Cytotoxicity} = 1 - (\text{cpm test}/\text{cpm control}) \times 100$$

wherein cpm control represents counts per minute of target cells cultured with untreated monocytes and CPN test represents counts/minute of target cells cultured with cytokine-treated monocytes.

Cytokine treatment of monocyte cultures consisted of IL-7 (100 ng/ml), GM-CSF (100 ng/ml), or LPS (10 µg/ml). The data presented in Table 6 are arranged as the % cytotoxicity of monocytes cultured in cytokine or LPS compared to % cytotoxicity of monocytes cultured in medium alone. These data are presented as mean±SEM (standard error of the mean) of six replicate cultures. Counts per minute (cpm) for A375 cells cultured with no monocytes and A375 cells cultured with non-stimulated monocytes were:

For Experiment 1: 19,286 and 18,903;

For Experiment 2: 34,655 and 28,119; and

For Experiment 3: 39,303 and 31,491.

The data are presented in Table 6.

TABLE 6

| | % Cytoxicity | | |
|---|---|---|---|
| Stimulus | Experiment 1 | Experiment 2 | Experiment 3 |
| IL-7 | 31.4 ± 1.5 | 60.3 ± 2.5 | 37.6 ± 3.3 |
| GM-CSF | 75.2 ± 6.5 | 49.3 ± 3.4 | 40.5 ± 1.9 |
| LPS | 69.9 ± 6.0 | 58.4 ± 1.9 | 60.4 ± 4.3 |

These data demonstrate that IL-7 significantly enhanced monocyte tumoricidal activity by inducing a mean of 43% cytotoxicity in three experiments. These data compare favorably to a mean cytotoxicity of 55% and 63% with GM-CSF and LPS-cultured monocytes, respectively. Inasmuch as GM-CSF contains known tumoricidal activity to a wide variety of tumors, these data show that IL-7 also induces tumoricidal activity to a wide variety of tumors.

EXAMPLE 10

This example illustrates the ability of IL-7 to induce IL-6 secretion in whole blood cultures. Whole blood cultures were obtained by obtaining heparinized whole blood cultured in polypropylene tubes (Falcon, Becton Dickinson, Mountain View Calif.) at 2 ml/tube. Various stimuli were added to the whole blood cultures. After 24 hours of incubation at 37° C. in a humidified atmosphere of 5% C)2 in air, plasma was separated by centrifugation at 700×g for 10 minutes and filtered through a 0.45 µMillipore filter. Plasma cytokine levels were determined by cytokine-specific ELISA assays. This procedure is described in greater detail in Strieker et al., *J. Leukocyte Biol.* 47:366 (1990). Strieker et al. also describes the ability of LPS to induce IL-6 and TNFα secretion in whole blood culture. The whole blood culture system more closely resembles in vivo conditions than isolated PBMC or monocyte cultures and avoids any artifact effects that may be attributed to cell preparation, culture medium, FCS (fetal calf serum), or adherence to plastic.

We obtained whole blood cultures and supplemented them with either IL-1β (100 ng/ml), IL-7 (100 ng/ml), LPS (10 µg/ml), or nothing (control). After 24 hours incubation, plasma was isolated and assessed for the presence of IL-1α, IL-1β, IL-6 and TNFα by cytokine-specific ELISA assays. As shown in Table 7 (below), cytokines were not detected in control whole blood cultured for 24 hours in the absence of a stimulus. As previously reported in Strieker et al., LPS was a potent stimulus for cytokine secretion in whole blood cultures. In addition, high levels of IL-6 were detected in the plasma from whole blood stimulated with IL-7 or IL-1β.

TABLE 7

| Stimulus | Cytokine production (pg/ml) | | | |
|---|---|---|---|---|
| | IL-1α | IL-1β | IL-6 | TNFα |
| Medium | <1 | <5 | <3 | <2 |
| IL-1β | <1 | — | 432 | 5 |
| IL-7 | 110 | 209 | 801 | 9 |
| LPS | 11100 | 7542 | 9954 | 6870 |

However, IL-7 was a relatively poor stimulus for IL-1α, IL-1β or TNFα production in whole blood when compared to LPS.

EXAMPLE 11

This example illustrates the effect of IL-7 on MIP-1β gene expression in human monocytes. MIP-1β is macrophage inflammatory prin-1. MIP-1β has been found to be a potent chemotactic stimulus. Other biological properties of human MIP-1β are not well understood. However, murine MIP-1β is known to induce acute inflammation and attract neutrophils (Wolpe et al., *J. Exp. Med.* 167:570 (1988)) and to synergize with murine macrophage-colony stimulating factor (M-CSF) and murine GM-CSF to enhance colony formation by murine bone marrow granulocyte/macrophage precursor cells (Broxmeyer et al., *J. Exp. Med.* 170:1583 (1989)).

First we cloned human MIP-1β cDNA from PMA+PHA-Stimulated Human PBTs (peripheral blood thymocytes) using PCT technology. The sequence of the primers used (5' oligonucleotide: 5'-ATATGGTACCGCACCAATGGGCTCAGAC-3'; 3'oligonucleotide: 5'-ATATGCGGCCGCTCAGTTCAGTTCCAGGTC-3') as determined from cDNA clone pAT 744 (Zipfel et al., *Proc. Natl. Acad. Sci. U.S.A.* 142:1582 (1989)). The 5' end of the clone encodes a mature amino terminus of human MIP-1β, while the termination codon is the 3' end of the clone. The amplified product was digested with restriction enzyme Asp 718 and NotI at restriction sites that had been included in the primers. The amplified product was cloned into Bluescript SK (Stratagene La Jolla, Calif.) plasmid. The plasmid was digested with Asp 718. Antisense RNA probes were generated using T3 RNA polymerase.

As was previously demonstrated for the MIP-1β gene, LPS (10 µg/ml) induces human MIP-1β mRNA. However, monocytes cultured in medium alone for four hours contained no detectable human MIP-1β mRNA. The kinetics of human MIP-1β mRNA production are similar to those seen for IL-1β and TNFα genes. This, LPS is a potent stimulator of human MIP-1β gene expression in purified human monocytes.

We assessed the ability of IL-7 to stimulate human MIP-1β gene expression in human monocytes. We found that IL-7 is capable of inducing MIP-1βmRNA in these cells. The concentration of IL-7 required to induce human MIP-1β gene expression was from about 10 ng/ml to about 100 ng/ml.

The kinetics of induction of human MIP-1β mRNA by IL-7 are similar to the kinetics of IL-6 induction by IL-7 because human MIP-1β mRNA was detectable within one hour of IL-7 incubation. Further, the amount of human MIP-1β mRNA induced by IL-7 was approximately 10%–20% of that induced by LPS.

EXAMPLE 12

This example illustrates the effect of IL-7 to induce human MIP-1β mRNA in human PBTs. Human PBTs were incubated with 100 ng/ml IL-7 for varying amounts of time. PBTs stimulated with 100 ng/ml of IL-7 for five or 12 hours failed to express detectable human MIP-1β mRNA. PBT cells incubated with 10 ng/ml PMA plus 500 ng/ml ionomycin (a positive control) for four hours showed strong induction of human MIP-1β mRNA. Analysis of the T cells stimulated with IL-7 showed an increase in cell surface expression of IL-2 receptor alpha-chains. These data indicate that the T cells were competent to respond to IL-7. These data further indicate that IL-7 signals differently in T cells and monocytes.

EXAMPLE 13

This example illustrates the ability of IL-4 to inhibit the induction of MIP-1β mRNA by LPS and IL-7. Monocytes were treated with 10 µg/ml LPS, or 100 ng/ml IL-7 with or without 100 ng/ml IL-4. After four hours of incubation, mRNA was isolated and analyzed as described in Example 11. IL-4 treatment alone was unable to induce human MIP-1β mRNA in monocytes. However, IL-4 inhibited the induction of human MIP-1β mRNA by LPS and IL-7. Similar inhibition of human MIP-1β mRNA induction by IL-7 was seen with 10 ng/ml IL-4, while 1 ng/ml IL-4 or lower amounts of IL-4 had little or no effect.

EXAMPLE 14

Figure 3B:
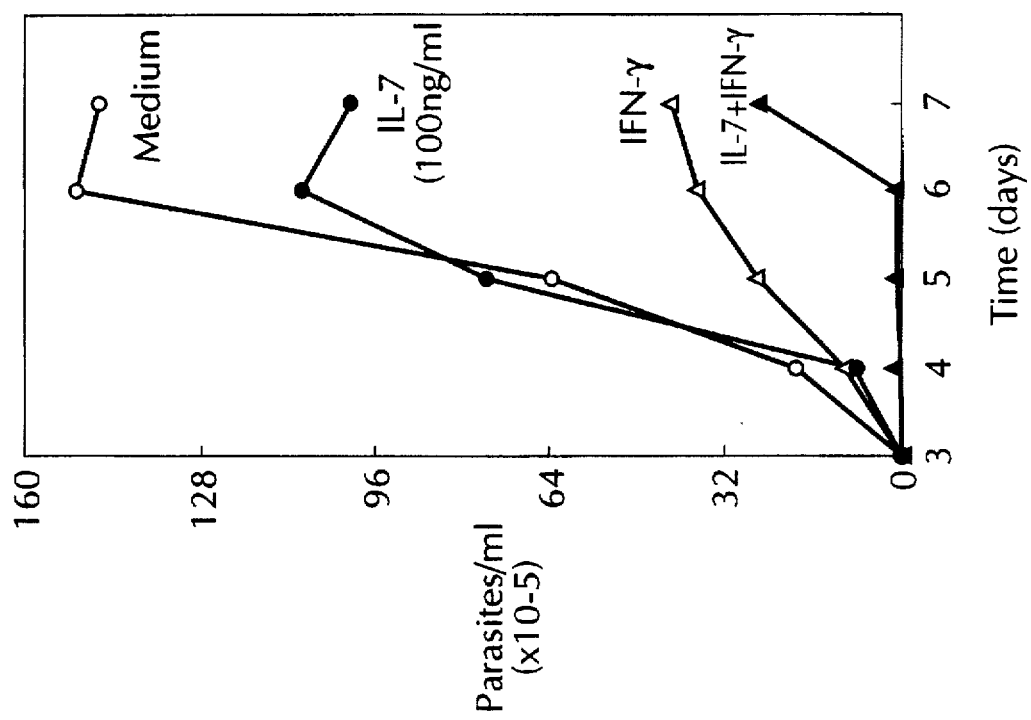
FIGS. 3A and 3B show antimicrobial activity of two doses of IL-7 (10 ng/ml, FIG. 3A; and 100 ng/ml, FIG. 3B) IFN-γ and the combination of IL-7 and IFN-γ against the protozoan parasite T. cruzi. The combination of IL-7 and IFN-γ showed synergistic antimicrobial activity.
Figure 3A:
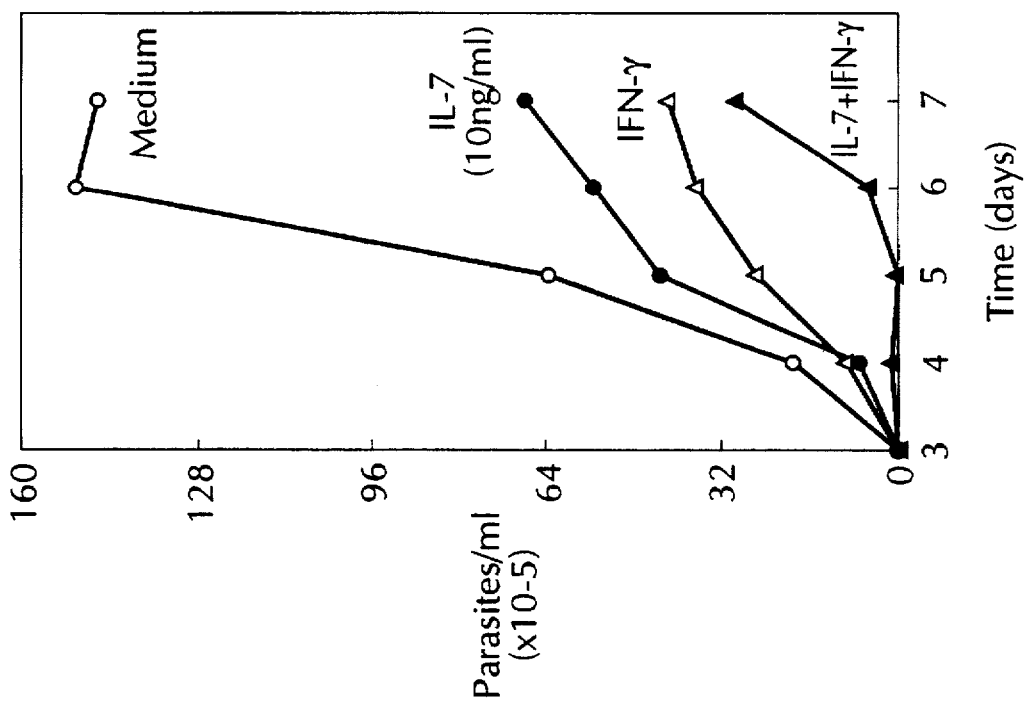

This example further illustrates antimicrobial activity of IL-7 alone and synergistic antimicrobial activity of IL-7 in combination with IFN-γ. Reed et al., *J. Exp. Med.* 166:1734–46 (1987) describes the antimicrobial activity of GM-CSF and interferon-γ (IFN-γ) in a *T. cruzi* model. Reed et al. found that IFN-γ exhibited potent antimicrobial activities on this protozoan parasite. However, Reed et al. noted that recruitment of peritoneal macrophages was required. We investigated whether IL-7 alone and IL-7 in combination with INF-γ would also exhibit antimicrobial activity using *T. cruzi* as a test organism. We followed the *T. cruzi* model procedures described in Reed et al. We used two doses of IL-7, 10 ng/ml and 100 ng/ml. The IFN-γ dose was 100 ng/ml. The results of this experiment are shown in FIGS. 3A and 3B. The data presented in FIGS. 3A and 3B show that both IL-7 and IFN-γ exhibited antimicrobial activity against *T. cruzi*. IFN-γ exhibited slightly more antimicrobial activity than IL-7. However, a combination of IL-7 and IFN-γ significantly enhanced the antimicrobial activity of both cytokines. When using the 100 ng/ml dose of IL-7 and 100 ng/ml of IFN-γ, the combination virtually eliminated the presence of *T. cruzi* for up to six days. These data illustrate synergistic antimicrobial activity from the combination of IL-7 and IFN-γ.

EXAMPLE 15

This example illustrates the ability of IL-7 to regulate monocyte cell surface markers. Monocytes are key players in a host response to infection. Cell surface markers on monocytes are essential for antigen presentation and for cell adhesion. Further, cell surface markers are thought to be crucial to cognate cell—cell interactions and cell trafficking. Therefore, regulation of surface molecule expression (such as MHC and cell adhesion molecules on monocytes) is fundamentally important for the host immune response to infection, and particularly for monocyte response to microbial infection.

We found that IL-7 enhances HLA-DR expression and induces CD23 on human monocytes. Both HLA-DR and CD23 are monocyte cell surface markers.

Human monocytes were purified from PBMC from healthy donors by countercurrent elutriation, as described in Example 1. Elutriated cells were 90–95% monocytic morphology as determined by microscopic examination of Giemsa-stained cytospin preparations and 80–85% CD14+ as determined by flow cytometry. Flow cytometry was performed using a FACScan (Becton Dickinson, Mountain View, Calif.). Human cell surface molecules were identified by murine monoclonal antibodies against the human cell surface molecules. Particularly, HLA-DR was identified by the L243 monoclonal antibody (MAb), CD23 cell surface molecule by the MHM6 Mab, the CD14 cell surface molecule by the UCHM1, the ICAM-1/CD54 cell surface molecule by the LB2, and the LFA-1/CD11a by the MHM24 Mab.

Human monocytes were cultured for 40 hours with 10 ng/ml of IL-7, IL-4, IFN-γ or GM-CSF, and then assessed for cell surface molecule expression (HLA-DR and CD23) by flow cytometry. All four cytokines were able to augment HLA-DR and CD23 expression, although to varying degrees. IL-7 was the weakest stimulus for both cell surface molecules of the four cytokines tested. Gross response analysis of the cytokines indicated that, whereas 100 ng/ml of IL-7 was required to augment CD23 expression, only 0.1 ng/ml of IL-7 was required for the enhancement of HLA-DR expression.

Figure 4A:
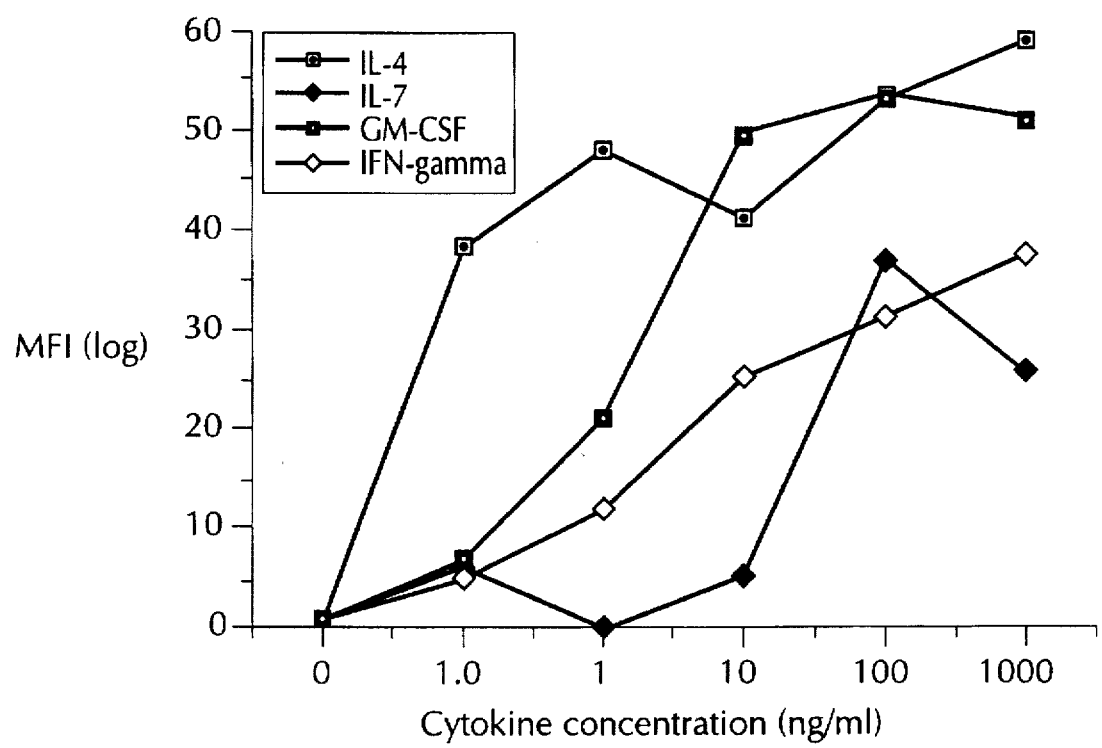
FIGS. 4A and 4B show the effect of cytokines IL-7, IL-4, GM-CSF and IFN-γ on monocyte expression of cell surface markers CD23 (FIG. 4A) and HLA-DR (FIG. 4B). IL-7 was found to enhance HLA-DR and induce CD23 expression on monocytes.
Figure 4B:
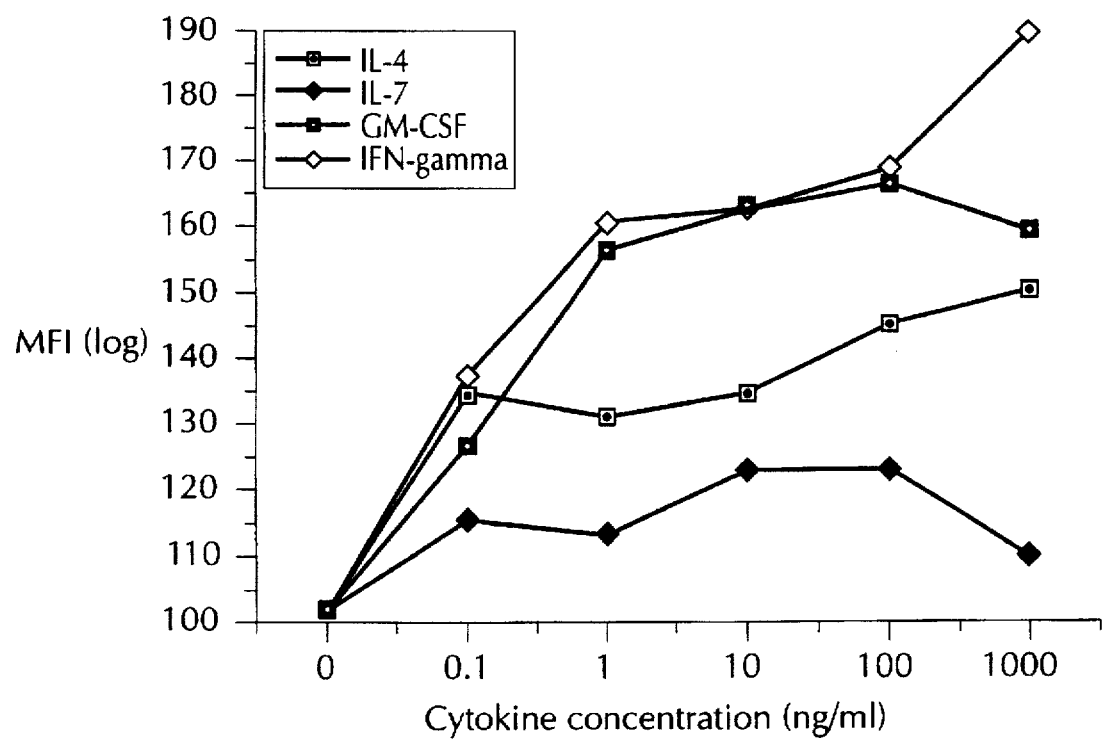

IL-7 was also the only cytokine of the four tested (the other being IL-4, IFN-γ and GM-CSF) to up-regulate CD14 expression. In contrast, GM-CSF down-regulated CD 14 expression. IFN-γ and GM-CSF up-regulated the cellular adhesion molecules ICAM-1 and LFA-1. IL-7 up-regulated ICAM-1 in the absence of any change in LFA-1 levels. The effect of the four cytokines on monocyte CD23 expression is shown in FIG. 4A. The effect of the four cytokines on monocyte HLA-DR expression is shown in FIG. 4B. A summary of the effect of IL-4, IL-7, IFN-γ and GM-CSF, along with a medium control, is shown in Table 8.

TABLE 8

| Stimulus | CD23 Exp. 1 | CD23 Exp. 2 | CD14 Exp. 1 | CD14 Exp. 2 | LFA-1 Exp. 1 | LFA-1 Exp. 2 | ICAM-1 Exp. 1 | ICAM-1 Exp. 2 |
|---|---|---|---|---|---|---|---|---|
| Medium | 17 | 30 | 450 | 250 | 400 | 250 | 180 | 50 |
| IL-4 | 80 | 120 | 400 | 65 | 350 | 250 | 250 | ND |
| IL-7 | 65 | 45 | 1400 | 700 | 360 | 250 | 400 | 130 |
| IFN-γ | 25 | 35 | 470 | 250 | 830 | 450 | 350 | ND |
| GM-CSF | 300 | 45 | 150 | 55 | 650 | 300 | 500 | 126 |

In summary, IL-4, IL-7, IFN-γ and GM-CSF all enhanced CD23 expression; IL-7 enhanced CD14 and ICAM-1 expression; GM-CSF inhibited CD-14 expression; and IFN-γ enhanced LFA-1 and ICAM-1 expression. The data further indicate that IL-7 provides significant antimicrobial and antitumor activity mediated through activated monocytes/macrophages.

From the foregoing, it will be appreciated that IL-7 alone and IL-7 in combination with IFN-γ has a broad spectrum of antimicrobial and antitumor activity as evidenced by its effects on macrophages and its antitumor and antimicrobial effects on a number of cancer cell lines and microbes. Therefore, other embodiments, activities and processes are included within the scope of the present invention, including additional antitumor effects on other cancer cell lines and types and additional antimicrobial activity on a wide variety of other families, genera and species of microbial pathogens.

We claim:

1. A method of treating a mammal comprising administering to said mammal an amount of IL-7 effective to stimulate an immune response by monocytes/macrophages to become cytotoxic, wherein said IL-7 is in a pharmaceutically acceptable carrier.

2. The method of claim 1 wherein the IL-7 is human IL-7.

3. The method of claim 1, wherein the amount of IL-7 administered is from about 1 μg/kg/day to about 100 μg/kg/day.

* * * * *